(12) United States Patent
Tom (10) Patent No.: US 7,211,063 B2
(45) Date of Patent: May 1, 2007

(54) PRESSURE SENSOR FOR THERAPEUTIC DELIVERY DEVICE AND METHOD (75) Inventor: Curtis P. Tom, Menlo Park, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 483 days.

(21) Appl. No.: 10/749,327

(22) Filed: Dec. 30, 2003

(65) Prior Publication Data
US 2004/0225298 A1 Nov. 11, 2004

Related U.S. Application Data (63) Continuation of application No. 10/347,567, filed on Jan. 17, 2003, now Pat. No. 6,695,808, which is a continuation of application No. 09/816,708, filed on Mar. 23, 2001, now abandoned.

(60) Provisional application No. 60/191,610, filed on Mar. 23, 2000.

(51) Int. Cl.
A61M 31/00 (2006.01)
(52) U.S. Cl. .............. 604/65; 604/66; 604/67; 607/120; 607/122; 606/108; 600/466
(58) Field of Classification Search .............. 604/65, 604/66, 67; 607/120, 122; 606/108; 600/466
See application file for complete search history.

(56) References Cited
U.S. PATENT DOCUMENTS
3,773,034 A 11/1973 Burns et al.
3,952,742 A 4/1976 Taylor
4,163,204 A 7/1979 Sado et al.

(Continued)

FOREIGN PATENT DOCUMENTS
EP 0 442 015 2/1990

(Continued)

OTHER PUBLICATIONS
Padua et al., "Basic fibroblast growth factor is cardioprotective in ischemia-reperfusion injury" Molecular and Cellular Biochemistry 143: 129-135 (1995).

(Continued)

Primary Examiner—Steven J. Ganey
(74) Attorney, Agent, or Firm—Jones Day (57) ABSTRACT The present invention is an apparatus for treating a selected patient tissue or organ region, at the surface of such region. The apparatus has an accessing tool for accessing the patient region, the tool having a distal end, and a proximal end at which the tool can be manipulated to place the distal end adjacent to the patient region. The apparatus also has a probe carried on the distal end and defining a contact surface that may be urged against the patient region thereby creating contact pressure. A pressure transducer is operatively coupled to the probe and is capable of producing a measurable response to the contact pressure. A monitoring device is operatively connected to the pressure transducer, for determining the contact pressure. An effector is operatively disposed on the probe for producing a given effect on the patient region when the effector is activated, and an activator operatively connected to the effector, by which the effector can be activated.

27 Claims, 7 Drawing Sheets

U.S. PATENT DOCUMENTS

| | | |
|---|---|---|
| 4,296,100 A | 10/1981 | Franco |
| 4,320,392 A | 3/1982 | Giovinazzo et al. |
| 4,469,091 A | 9/1984 | Slanetz, Jr. |
| 4,531,936 A | 7/1985 | Gordon |
| 4,657,536 A | 4/1987 | Dorman |
| 4,736,640 A | 4/1988 | Hooks |
| 4,763,534 A | 8/1988 | Hager |
| 4,770,653 A | 9/1988 | Shturman |
| 4,847,586 A | 7/1989 | Tanaga et al. |
| 4,904,184 A | 2/1990 | Murphy et al. |
| 4,911,148 A | 3/1990 | Sosnowski et al. |
| 4,946,442 A | 8/1990 | Sanagi |
| 4,994,033 A | 2/1991 | Shockey et al. |
| 5,061,273 A | 10/1991 | Yock |
| 5,185,004 A | 2/1993 | Lashinski |
| 5,203,772 A | 4/1993 | Hammerslag et al. |
| 5,244,460 A | 9/1993 | Unger et al. |
| 5,339,799 A | 8/1994 | Kami et al. |
| 5,341,687 A | 8/1994 | Stan |
| 5,385,148 A | 1/1995 | Lesh et al. |
| 5,396,887 A | 3/1995 | Imran |
| 5,414,940 A | 5/1995 | Sturdevant |
| 5,419,777 A | 5/1995 | Hofling |
| 5,429,006 A | 7/1995 | Tamori |
| 5,489,575 A | 2/1996 | Lee et al. |
| 5,499,971 A | 3/1996 | Shapland et al. |
| 5,507,724 A | 4/1996 | Hofmann et al. |
| 5,520,188 A | 5/1996 | Hennige et al. |
| 5,526,703 A | 6/1996 | Aslam et al. |
| 5,553,500 A | 9/1996 | Grahn et al. |
| 5,569,160 A | 10/1996 | Sauer et al. |
| 5,569,217 A | 10/1996 | Luther |
| 5,571,215 A | 11/1996 | Sterman et al. |
| 5,578,766 A | 11/1996 | Kondo |
| 5,583,303 A | 12/1996 | Franz |
| 5,591,195 A | 1/1997 | Taheri et al. |
| 5,604,314 A | 2/1997 | Grahn |
| 5,645,531 A * | 7/1997 | Thompson et al. ............ 604/67 |
| 5,653,684 A | 8/1997 | Laptewicz et al. |
| 5,661,133 A | 8/1997 | Leiden et al. |
| 5,662,124 A | 9/1997 | Wilk |
| 5,693,029 A | 12/1997 | Leonhardt |
| 5,698,531 A | 12/1997 | Nabel et al. |
| 5,725,523 A | 3/1998 | Mueller |
| 5,733,280 A | 3/1998 | Avitall |
| 5,755,714 A | 5/1998 | Murphy-Chutorian |
| 5,797,870 A | 8/1998 | March et al. |
| 5,797,960 A | 8/1998 | Stevens et al. |
| 5,820,592 A | 10/1998 | Hammerslag |
| 5,827,216 A | 10/1998 | Igo et al. |
| 5,830,993 A | 11/1998 | Blecha et al. |
| 5,833,658 A | 11/1998 | Levy et al. |
| 5,840,031 A | 11/1998 | Crowley |
| 5,840,059 A | 11/1998 | March et al. |
| 5,840,062 A | 11/1998 | Gumaste et al. |
| 5,843,050 A | 12/1998 | Jones et al. |
| 5,846,221 A | 12/1998 | Snoke et al. |
| 5,855,577 A | 1/1999 | Murphy-Chutorian et al. |
| 5,857,464 A | 1/1999 | Desai |
| 5,860,953 A | 1/1999 | Snoke et al. |
| 5,871,495 A | 2/1999 | Mueller |
| 5,876,373 A | 3/1999 | Giba et al. |
| 5,882,332 A | 3/1999 | Wijay |
| 5,885,272 A | 3/1999 | Aita et al. |
| 5,886,615 A | 3/1999 | Burgess |
| 5,891,133 A | 4/1999 | Murphy-Chutorian |
| 5,925,012 A | 7/1999 | Murphy-Chutorian et al. |
| 5,931,831 A | 8/1999 | Linder |
| 5,935,063 A | 8/1999 | Nguyen |
| 5,941,845 A | 8/1999 | Tu et al. |
| 5,941,868 A | 8/1999 | Kaplan et al. |
| 5,964,754 A | 10/1999 | Osypka |
| 5,971,983 A | 10/1999 | Lesh |
| 5,989,700 A | 11/1999 | Krivopal |
| 5,993,443 A | 11/1999 | Murphy-Chutorian et al. |
| 5,997,525 A | 12/1999 | March et al. |
| 6,004,269 A | 12/1999 | Crowley et al. |
| 6,012,457 A | 1/2000 | Lesh |
| 6,024,703 A | 2/2000 | Zanelli et al. |
| 6,063,022 A | 5/2000 | Ben-Haim |
| 6,133,233 A | 10/2000 | Ross et al. |
| 6,161,543 A | 12/2000 | Cox et al. |
| 6,171,276 B1 * | 1/2001 | Lippe et al. .................. 604/65 |
| 6,171,303 B1 | 1/2001 | Ben-Haim et al. |
| 6,179,809 B1 | 1/2001 | Khairkhahan et al. |
| 6,183,444 B1 | 2/2001 | Glines et al. |
| 6,224,584 B1 | 5/2001 | March et al. |
| 6,237,605 B1 | 5/2001 | Vaska et al. |
| 6,309,370 B1 * | 10/2001 | Haim et al. .................. 607/120 |
| 6,309,375 B1 | 10/2001 | Glines et al. |
| 6,314,962 B1 | 11/2001 | Vaska et al. |
| 6,314,963 B1 | 11/2001 | Vaska et al. |

FOREIGN PATENT DOCUMENTS

| | | |
|---|---|---|
| WO | WO 96/32129 | 10/1996 |
| WO | WO 97/25101 | 7/1997 |
| WO | WO 97/47253 | 12/1997 |
| WO | WO 99/39624 | 8/1999 |
| WO | WO A 9939624 | 8/1999 |
| WO | WO 00/57895 | 10/2000 |

OTHER PUBLICATIONS

Shi et al., "PR-39, a proline-rich antibacterial peptide that inhibits phagocyte NADPH oxidase activity by binding to Src homology 3 domains of p47phox" Proc. Natl. Acad. Sci. 93:6014-6018 (1996).

Uchida et al., "Angiogenic therapy of acute myocardial infarction by intrapericardial injection of basic fibroblast growth factor and heparin sulfate: An experimental study" Am. Heart J., 130:1182-1188 (1995).

Unger et al. "Basic fibroblast growth factor enhances myocardial collateral flow in a canine model" Am J. Physiol., 266:H1577-H1595 (1994).

Walterberger et al., "Ischemia-Induced Transplant Arteriosclerosis in the Rat" Arteriosclerosis, Thrombosis and Vascular Biology 16(12):1516-1523 (1996).

Xiaobing, et al. "Ischemia and Reperfusion reduce the Endogenous Basic Fibroblast Growth Factor (bf GF) in Rat Skeletal Muscles" Chinese Medical Journal 108(9): 699-703, (1995).

* cited by examiner

PRESSURE SENSOR FOR THERAPEUTIC DELIVERY DEVICE AND METHOD

CROSS-REFERENCE TO RELATED APPLICATIONS

This application is a continuation of application Ser. No. 10/347,567, filed Jan. 17, 2003 now U.S. Pat. No. 6,695,808, which is a continuation of application Ser. No. 09/816,708, filed Mar. 23, 2001, now abandoned, which claims the benefit of Provisional Application No. 60/191,610, filed Mar. 23, 2000, the disclosure of each of which is incorporated in their entirety herein by reference.

FIELD OF THE INVENTION

The present invention relates to an apparatus and method for affecting a body tissue, such as the heart, at the tissue surface, for purposes of injecting material into the tissue or otherwise stimulating a desired therapeutic effect on the tissue.

BACKGROUND OF THE INVENTION

Percutaneous catheter-based treatments of cardiovascular disease require that navigation of the catheter within the body be done with a mode of visualizing the catheter as it is moved within the body. The most popular mode of visualization is X-ray fluoroscopy, where an operator is able to monitor a radiopaque device as it travels within a body lumen, such as the cardiovascular system.

Recently, interventional procedures that require catheter navigation within the chambers of the heart have been developed; these include electrophysiological mapping and ablation and transmyocardial revascularization. These procedures also often require that the tip of the catheter be placed in contact with a wall of the beating heart in order to deliver the desired treatment safely. Potential complications of this procedure may be perforation of the wall when excessive force is applied or ineffective treatment due to poor tip contact. Under fluoroscopic guidance it is often difficult to assess when the catheter tip has reached the wall because live fluoroscopy does not visualize that wall itself, since it is not radiopaque. For the same reason, even after the catheter tip has reached the wall, it is difficult to determine whether the tip consistently remains in contact with the wall or if excessive force is applied to the wall. Finally, it is also difficult to determine whether the catheter tip is substantially perpendicular to the wall because fluoroscopy yields a two-dimensional image of the device in three-dimensional space.

Thus, for procedures where a medical instrument must be placed in firm but not excessive contact with an anatomical surface, there is an apparent need for a device which is able to provide information to the user of the instrument that is indicative of the existence and magnitude of the contact force. Furthermore, for procedures where the medical instrument must also be placed either perpendicular or at some selected angle to the anatomical surface, there is an apparent need for a device which is able to provide information to the user of the instrument that is indicative of the incident angle of the contact force with respect to the anatomical surface.

SUMMARY OF THE INVENTION

It is therefore an object of this invention to provide such a device for overcoming one or more of the above-mentioned problems.

It is another object of this invention to provide information to the user of a medical instrument, such as a catheter, that must be placed in contact with the surface of an anatomical structure, to increase the likelihood of safely delivering the desired treatment while reducing the possibility of inflicting perforation type injuries or providing inadequate treatment.

It is further an object of this invention to provide a method for generating information regarding whether the tip of a medical instrument, such as a catheter or probe, is in contact with a surface of a tissue or organ, and, if so, the magnitude of the contact force and the incident angle of the contact force with respect to the anatomical surface.

In summary, the present invention is an apparatus for treating a selected patient tissue or organ region, at the surface of such region. The apparatus may have an accessing tool for accessing the patient region, the accessing tool having a distal end, and a proximal end at which the tool can be manipulated to place the distal end adjacent to the patient region.

The apparatus may also have a probe carried on the distal end and defining a contact surface that may be urged against the patient region thereby creating contact pressure. The apparatus may further have at least one pressure transducer, wherein each pressure transducer may be operatively coupled to the probe and capable of producing a measurable response to the contact pressure experienced adjacent to the pressure transducer. A monitoring device may be operatively connected to each pressure transducer, for determining contact pressure. At least one effector may be provided, wherein each effector may be operatively disposed on the probe for producing a given effect on the patient region when the effector is activated. An activator may further be provided, which may be operatively connected to the effector, and by which the effector can be activated.

DETAILED DESCRIPTION OF THE INVENTION

Figure 1:
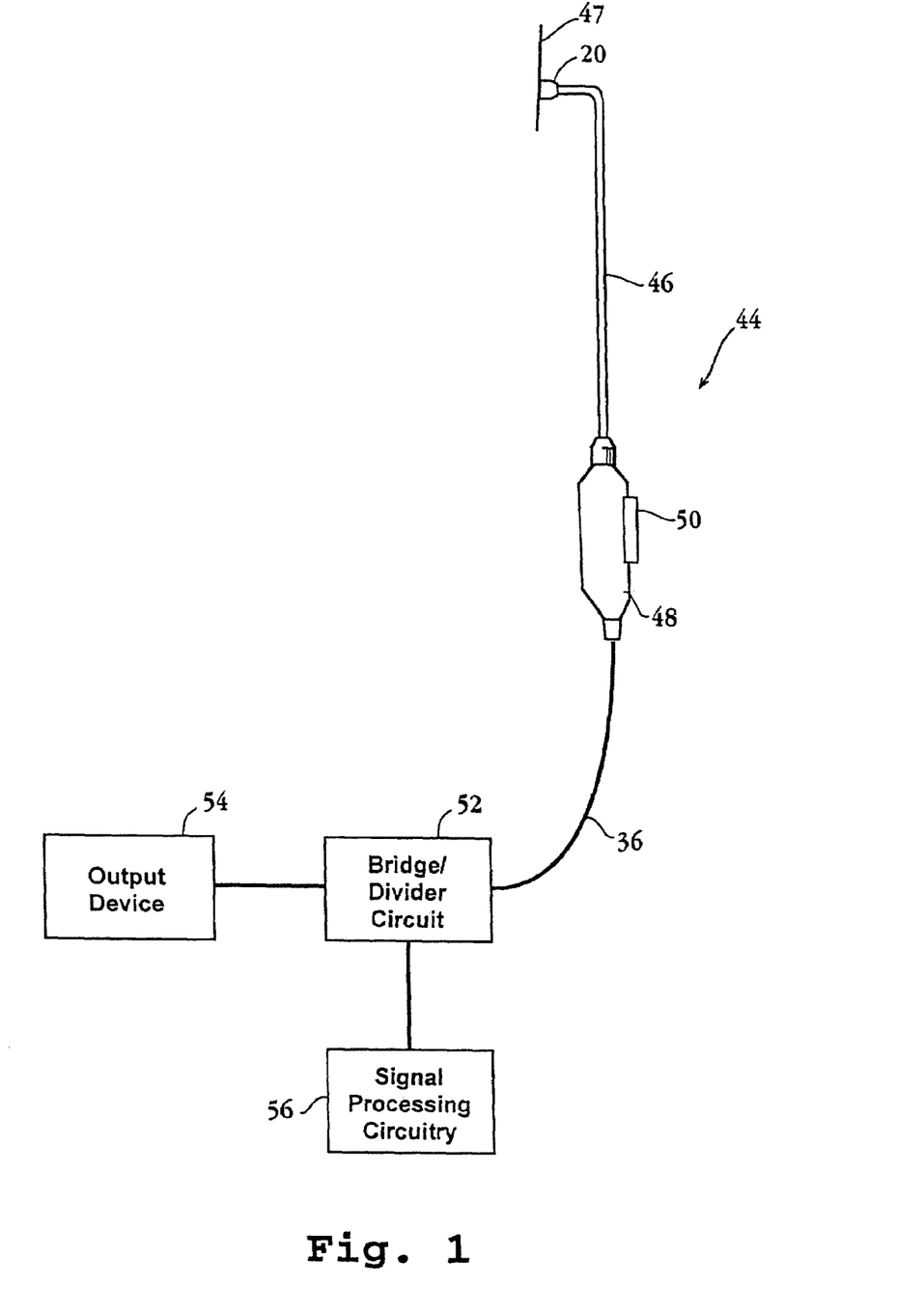
FIG. 1 illustrates the force contact transducer attached to a probing tool and monitoring circuitry.

FIG. 1 shows an apparatus 44 constructed according to the invention. The apparatus provides an assembly or tool 46, for accessing a patient tissue or organ region 47, and a sensor device 20, detailed below, for determining the pressure of the probe against the target tissue and, in some embodiments, the angle of contact between the probe and target tissue.

In general application, the assembly is used to access an internal target region, and to provide a therapeutic stimulus, such as injection of a therapeutic compound or gene, forming a laser channel, or introducing an injury, e.g., by ultrasonic waves, infrared radiation, or mechanical injury on or below the surface of the target region, e.g., to stimulate an angiogenic response in the target region. The therapeutic stimulus is preferably administered/provided through the assembly probe. The sensor device operates, in accordance with the invention, to provide information to the user about the position of the probe with respect to the target region, since the target region is generally not directly viewable by the user, e.g., physician.

In the embodiment shown, the medical instrument includes a rigid shaft 46, which may have a curved section, as shown in FIG. 1. Alternatively, the medical instrument is a flexible catheter, e.g., for delivery of a therapeutic stimulus to a target site within the vasculature or heart. The distal end of the shaft may be the base of the transducer, as shown in FIG. 1, or a separate element securely affixed to the base. A handle 48 is attached to the proximal end of the shaft or base. In one embodiment, the shaft is pivotally attached to the transducer base to permit the tip of the medical instrument to bend. The handle may include a control panel 50 for control of the instrument by the user. Also shown are a bridge divider, an output device 54, such as a display device, and signal processing circuitry 56 whose operation is described below.

While not detailed here, handle 48 may be designed to produce a selected therapeutic effect on target tissue, when a desired pressure and/or pressure contact angle is sensed between the probe and target tissue. The therapeutic effect may be, for example, the injection, by a needle or needleless injection system, of a solution or suspension of a therapeutic compound or gene, or a radiation or ultrasound injury produced by a light-carrying fiber or sonic device on the probe, or a mechanical injury produced by a mechanical tool on the probe. The apparatus may therefore be equipped, according to well-known devices, to provide an extendable needle, a light fiber, an extendable mechanical-injury device, or the like to produce the desired therapeutic effect, in response to a signal applied by the user to handle 48. That is, handle 48 may include structure for activating the therapeutic receptor at the distal end of the apparatus. In one embodiment, the therapeutic response is activated when the distal end of the apparatus is positioned against the target tissue with a desired pressure, that is, above a selected pressure threshold or within a desired pressure range, as determined from the pressure sensor device of the invention. In addition, angle of contact as sensed by the device may be employed as a variable to be considered in an automated triggering.

Figure 2:
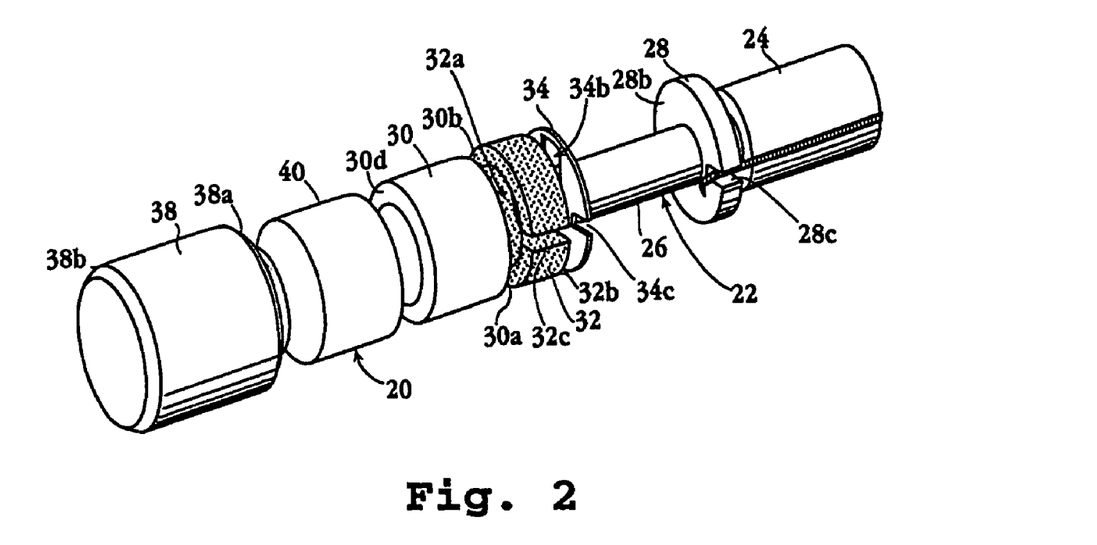
FIG. 2 is an exploded view of a force contact transducer constructed in accordance with embodiments of the invention.

FIG. 2 is an exploded view of a force contact transducer or device 20 constructed in accordance with embodiments of the invention. Device 20 includes an elongate, cylindrical base 22 that may be constructed of non-conductive material such as polycarbonate or a metallic conductive material such as surgical steel or similar material. The base has a larger diameter portion 24 that may serve as, or be attached to, a shaft of an associated medical instrument, such as a needle-delivery device or light fiber, in which the transducer is incorporated. Extending from the distal end of the larger diameter portion is a reduced diameter portion 26 (i.e., a reduced diameter shaft).

Attached to, or formed integrally with, the reduced diameter portion is a flange 28 that has a central opening 28a and one or more notches, such as notch 28c, formed in its outer edge. An upper surface 28b of the flange is electrically conductive (by placement of a not shown conductive layer and serves as one of the electrical conductors of the transducer. The details of the base are illustrated in FIG. 4.

Device 20 further includes a cap 30, which is generally cylindrical in shape and has an axial bore extending therethrough to define an inner wall. A plurality of rectangular feet 30b are formed on one end surface 30c of the cap, which surface acts as the second electrical conductor of the transducer. The cap is shown in more detail in FIG. 4.

Sandwiched between conducting surfaces 30c and 28b are: (i) a conductive or semi-conductive elastomer 32 that is preferably made of carbon loaded silicone rubber or other material with similar characteristics, and (ii) a thin, non-conducting insulating layer 34 that is preferably made of mylar, polyimide or other material which exhibits similar insulating or dielectric properties. Each of these components 32 and 34 has an opening 32a and 34a respectively formed therein so that these components may be received on the reduced diameter portion 26 of base 22. A lower surface of the insulating layer abuts against, but does not completely cover, conductor surface 28b, so that a lower surface 32b of the conductive elastomer is able to selectively make contact with conductor surface 28b based on a force applied to the transducer, as will be explained in more detail below.

Figures 4, 5:
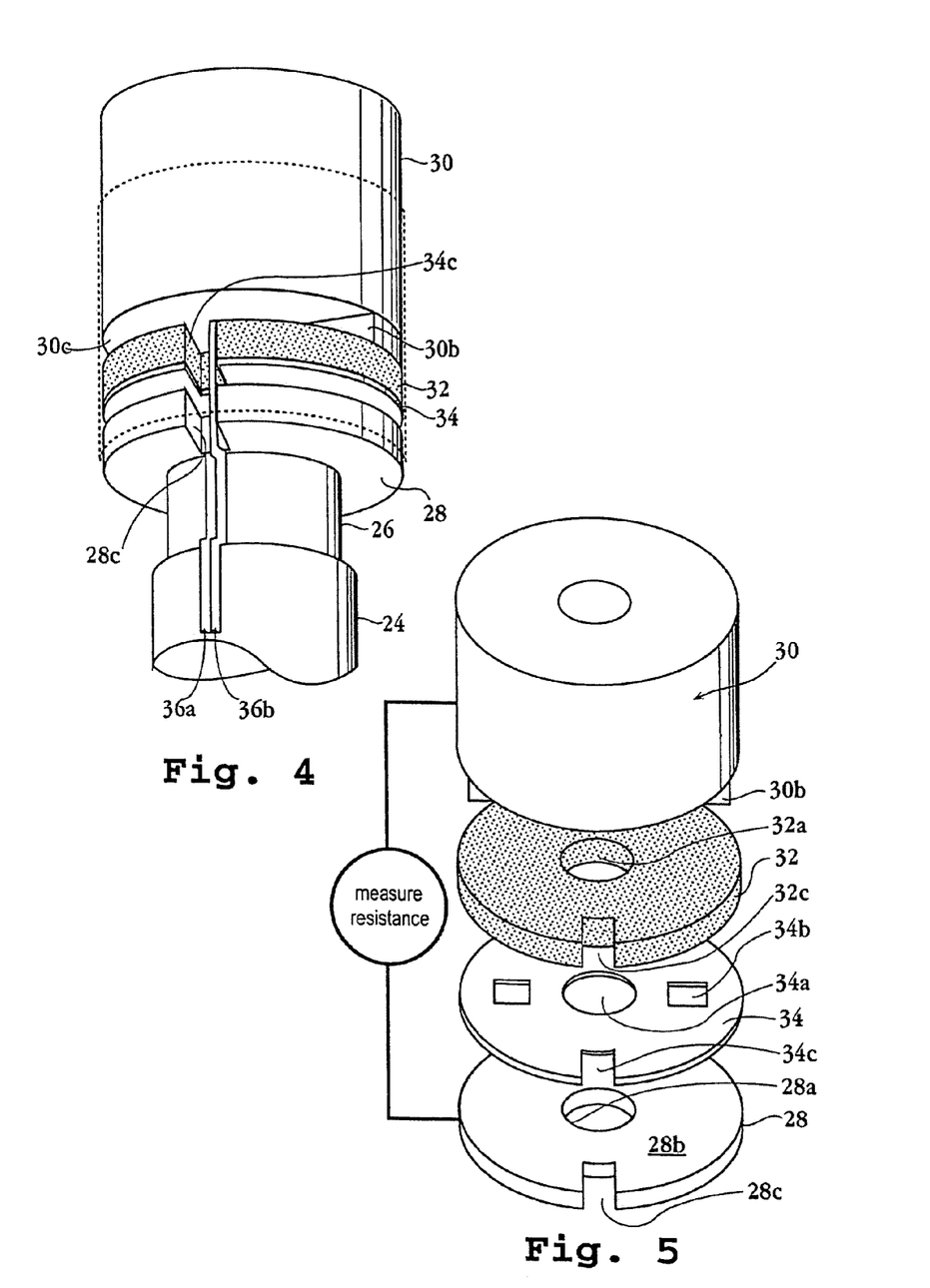
FIG. 4 illustrates a view of the cap region of the force contact transducer.
FIG. 5 illustrates a detailed exploded view of contact elements of the invention.

In the illustrated embodiment, this is accomplished by making opening 34b in the form of a slot, as seen best in FIG. 5. However, this is merely one example; other arrangements are possible. For example, the insulator may have a central opening and a plurality of radial arms providing a plurality of circumferential slots through which electrical contact may be selectively made between the elastomer and the confronting conductive surface 28b of flange 28.

Figure 3:
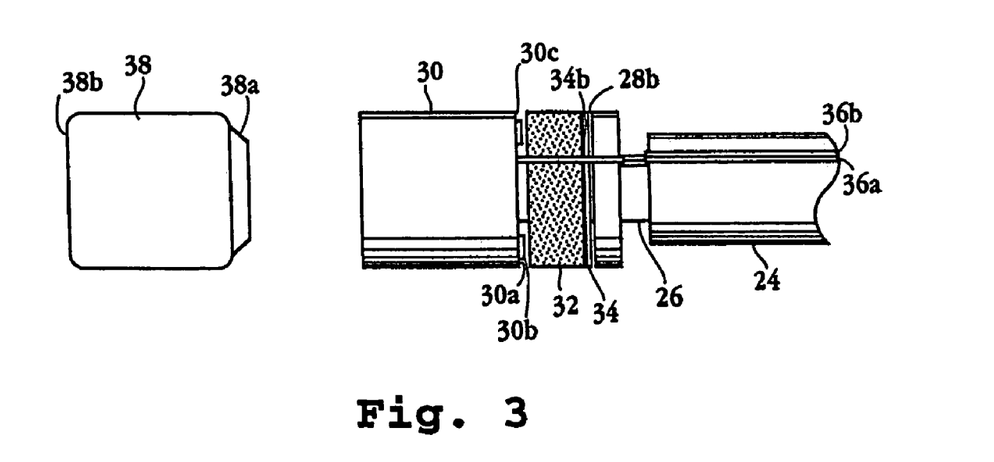
FIG. 3 illustrates a view of the cap and base of the force contact transducer.

Formed along the outer edge of insulator 34 is a notch 34c, which is aligned with notch 32c in elastomer 32 and slot 28c in flange 28, as seen particularly in FIGS. 3 and 4. The notches accommodate a pair of electrical leads 36a and 36b that are in electrical contact with conducting surfaces 28b and 30c, respectively, as shown in FIGS. 3 and 4.

Formed in an upper surface of the conductive elastomer is a plurality of indents or footprints that correspond to the feet 30b formed on conductive surface 30c of the cap. Each one of the feet 30b is adapted to fit securely within its complementary footprint to maintain constant contact between the conductive surface of cap 30 and the upper surface of conductive elastomer 32.

It is desirable to seal the components of the contact force transducer apparatus to prevent ingress of bodily or other fluids into the electrical regions of the apparatus. Furthermore, it is highly desired to seal the invention to prevent the egress of components from the contact force transducer apparatus. Accordingly, one skilled in the art would realize that numerous means for sealing the apparatus are possible. For example, a potting material may be introduced at component junctions so as to seal the device without interfering with its intended function. Alternatively and as discussed in detail below, a shroud or tip may be employed to seal the apparatus. Such sealing means may be preformed or formed in place, for example, by dipping an appropriately masked apparatus in a sealing compound to create a tip or shroud in place.

A tip element 38 may be employed to protect the cap. In one embodiment, the tip has a lower end 38a that is securely attached to an upper end of the cap, as shown in FIG. 2. In another embodiment, the tip extends over the cap-conductive elastomer-insulator assembly (not shown). In either case, when the tip is used, its outer surface 38b acts as the contact surface of the transducer. When the tip is not employed, the upper end of the cap is the contact surface. The transducer components including the tip in assembled form are shown in FIG. 2. When the tip is not used, upper end 30d serves as the contact surface of the transducer. The assembled transducer excluding the tip is shown in FIG. 3.

If desired, a suitable biologically compatible coating or cover 40 may be applied to the cap-conductive elastomer-insulator-flange assembly (and tip if included) to protect it and to prevent fluid ingress. Such a cover or coating, with portions broken away, is shown in FIG. 2.

A second embodiment of the invention (not shown) is similar to the first except that it further includes a thin insulator which fits between cap 30 and tip 38 to reduce the friction between these components and enable them to move relative to each other as the force applied to the contact surface of the transducer is varied.

In operation, an electrical excitation signal is generated in a bridge or divider circuit 52 (FIG. 1) and applied to the conductive surfaces or other electrical elements of the sensor described below. If a force below a predetermined threshold is applied to the contact surface of the transducer, the excitation signal will remain the same. However, if the applied force is just above the predetermined threshold, conductive elastomer 32, which is in constant contact with conductive surface 30c, will extend or be pushed through the openings or perforations in insulating layer 34 to make contact with conductive surface 28b. This causes the impedance between the two conductive surfaces to decrease, producing a change in the excitation signal which indicates that minimum contact has been made. As the applied force is further increased, the conductive elastomer compresses causing a further proportional drop in the impedance that, in turn, produces corresponding change in the excitation signal. Thus, the impedance and therefore the excitation signal varies with the magnitude of the applied force.

The bridge/divider circuit is in electrical communication with an output device 54 which may be in the form of an audio or visual device adapted to provide an information signal to the user indicative of whether the outer surface of the transducer has made contact, and, if so, the magnitude of the contact. The output device may take a variety of different forms. For example, an LED bar graph or other display capable of rendering a graphical or visual representation may be used to provide a continuous, quasi-continuous or discrete indication of the magnitude of a force applied to the contact surface of the transducer, from a minimum applied force indicative of minimum contact to a predetermined maximum. Alternatively, or in addition, a speaker or other audio device may be used to emit a sound when minimum contact is made and to emit proportionally louder sounds as the firmness of the contact increases.

The sensitivity of the excitation signal and hence the information signal may be adjusted in a number of different ways. One way is by using an elastomer with a different conductivity and/or compressibility. Another way is with electronic signal processing circuitry with adjustable amplification and filtering. Such a signal processing circuit (56) may be physically integrated with the bridge/divider circuit, or may be a separate circuit that is in electrical communication with the bridge/divider circuit, as illustrated in FIG. 1. The sensitivity of the signals (excitation and information) may also be adjusted by varying the size of the openings or perforations in the insulating layer, or by varying the thickness of the insulating layer. Larger perforations increase the sensitivity. In any case, the sensitivity of the transducer is set based on the desired contact force threshold and the minimum magnitude of change to be detected.

A flat transducer contact surface will generate less of an output signal if the tip is in contact with tissue surface at an oblique angle. On the other hand, a rounded or tapered contact surface will generate a greater output signal at an oblique angle of contact. Thus, the geometry of the contact surface may be tailored to provide feedback-about the perpendicularity of the contact between the medical instrument tip and the tissue surface. Optionally, the friction coefficient of the tip or exposed cap material at the contact surface may be altered to provide for shear force as the probe is situated upon a tissue surface in a way that a lateral force vector component manifests, assuming at least some of the thrust force applied creates a lateral force component. The less the friction between the contact surface and the tissue surface, the less the shear or lateral force component realized.

In another embodiment, a plurality of discrete transducers can be distributed on the tip of a medical instrument to provide further information regarding the perpendicularity of the contact. In the case of two transducers, each covers 180 degrees of the tip surface; in the case of three transducers, each covers 120 degrees, etc. The combined signal from the multiple transducers may be processed to provide, in addition to contact and magnitude information, angle of contact of information as well.

In another particularly preferred embodiment, a transducer, or transducers if contact angle sensing is sought, may comprise a thin double mylar film layered sandwich as described in Krivopal, U.S. Pat. No. 5,989,700, herein incorporated in its entirety by reference. Looking at FIG. 6, the instant invention differs from Krivopal in that sensor 60 has sensor elements 68 on a support 70 having an aperture 76 disposed in the center to permit tool shaft 64 to be disposed at a normal angle through the sensor or sensor array. Each individual sensor area is electrically accessible by leads 66.

Figure 6:
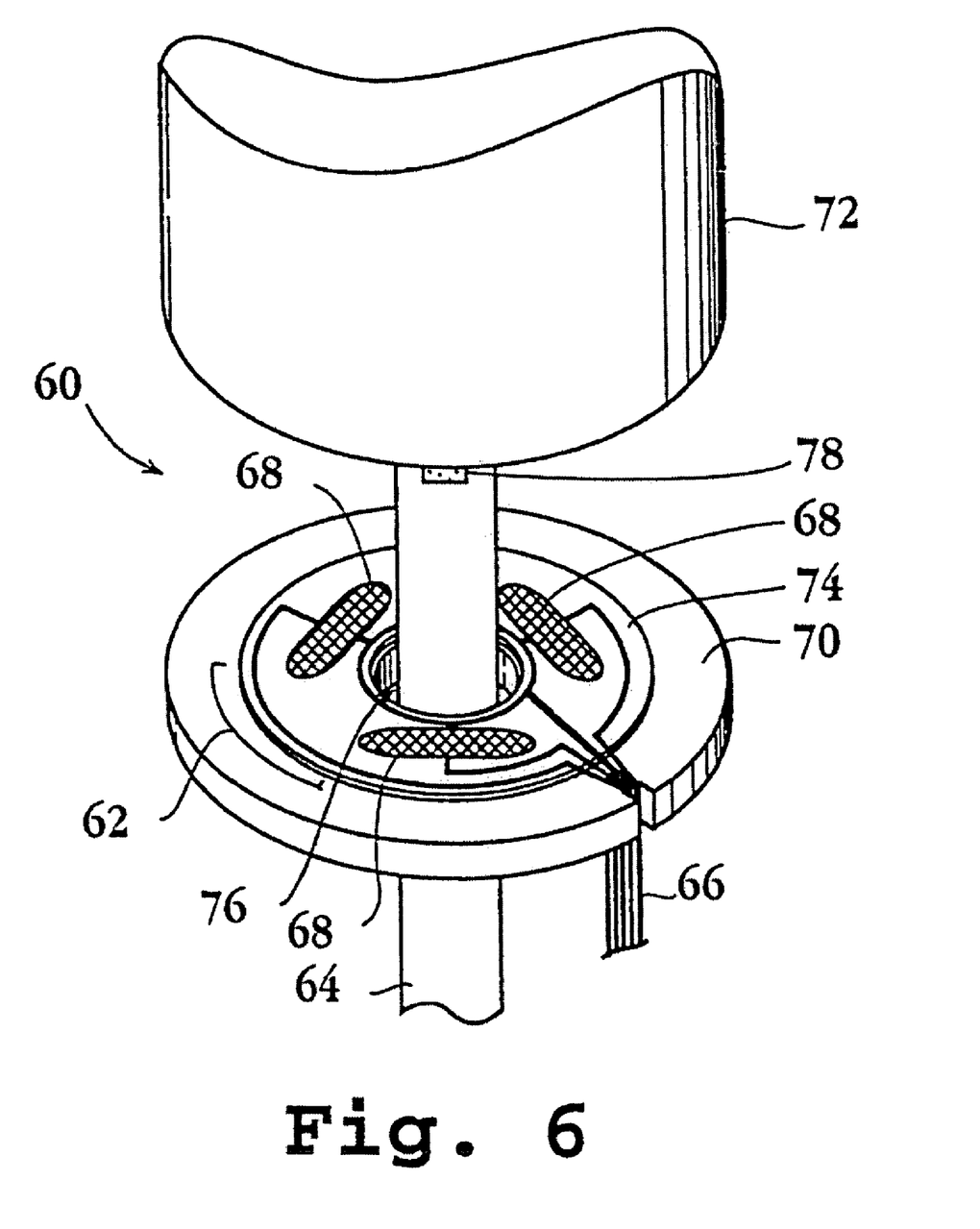
FIG. 6 illustrates one embodiment of the invention that employs a thin film transducer array disposed around a tool shaft.
Figure 7A:
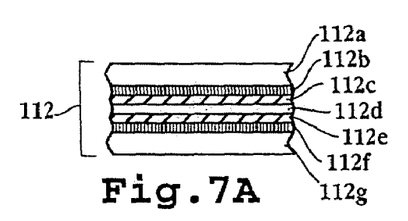
FIGS. 7A–7D illustrate embodiments of a transducer array and a single transducer.
Figure 7B:
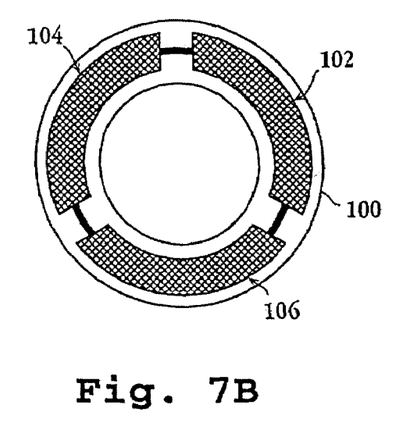
Figure 7C:
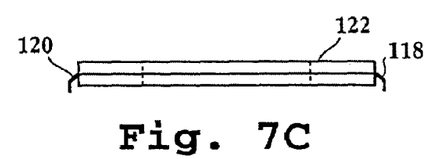
Figure 7D:
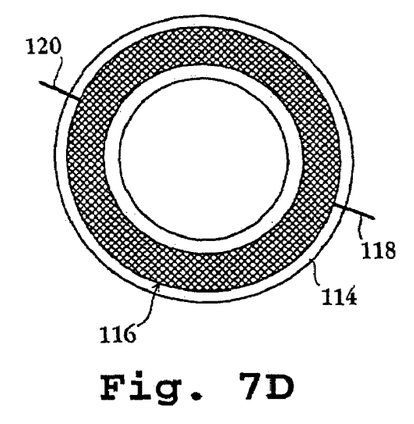

The sensor support 70 can either be rigid or elastic depending on the degree of flexibility sought in the device. Disposed above the sensor support is a resilient or elastomeric cap 72 which mechanically communicates the probe tip contact surface incident angle and total contact force downward to sensor 60. Cap 72 may further include protuberances 78 to focus the communicated force onto sensors 68.

The entire probe tip may be covered by a sheath, not shown. Alternatively, a transducer, such as a thin film transducer, may be positioned directly on the contact surface, thereby creating a superior contact surface. Alternatively, the probe may lack a cap element and thus directly expose a transducer, such as a thin film transducer, to a tip surface opposite the tip contact surface, or the transducer may itself comprise the tip surface, and thus the contact surface as well. Each of these embodiments just described may include one or more transducers so that incident angle as well as force may be detected.

Considering now the embodiments shown in FIGS. 7A–7D, a sandwich 112 has a top mylar film 112a (i.e., a primary layer of material), an upper conductive ink layer 112b applied to the lower surface region of the top mylar film 112a, an upper semiconductive ink layer 112c applied to the upper conductive ink layer 112b, an air gap 112d, a lower semiconductive ink layer 112e disposed upon a lower conductive ink layer 112f which is disposed on the upper surface of a bottom mylar film 112g (i.e., a secondary layer of material).

There may be an insulating ring or sections surrounding the above described ink sandwich to separate the upper mylar layer from the lower mylar layer thus creating the air-gap between the upper and lower semi-conductive ink layers. In the case of a multiple transducer array 100, several sandwich regions 102, 104, 106 may be arranged upon the plane created by the mylar film, each region being in electrical communication with the monitoring unit, and each region is independently responsive to the contact force present at the corresponding region of the contact surface of the probe thus providing a means of determining the incident angle of the contact force with respect to the tissue surface by comparing the individual responses of each transducer sandwich region.

Alternatively, each sandwich region 114 may be a separate mylar film sandwich 116, with each electrode 118, 120 individually in electrical communication with the monitor device.

In another embodiment, the pressure transducers may be a combination of a purely mechanical resilient device such as an elastomeric spacer, and a mechanical or electrical device for measuring the effect of the force upon the resilient device. Measurement may include a mechanical deflection of mechanically communicated information to a portion of the tool distal from the patient surface, or may be a switch or potentiometer mechanically operating above its inherent mechanical (frictional) resistance. Mechanically communicated deflection may be monitored and displayed to a user as described below.

Figure 8:
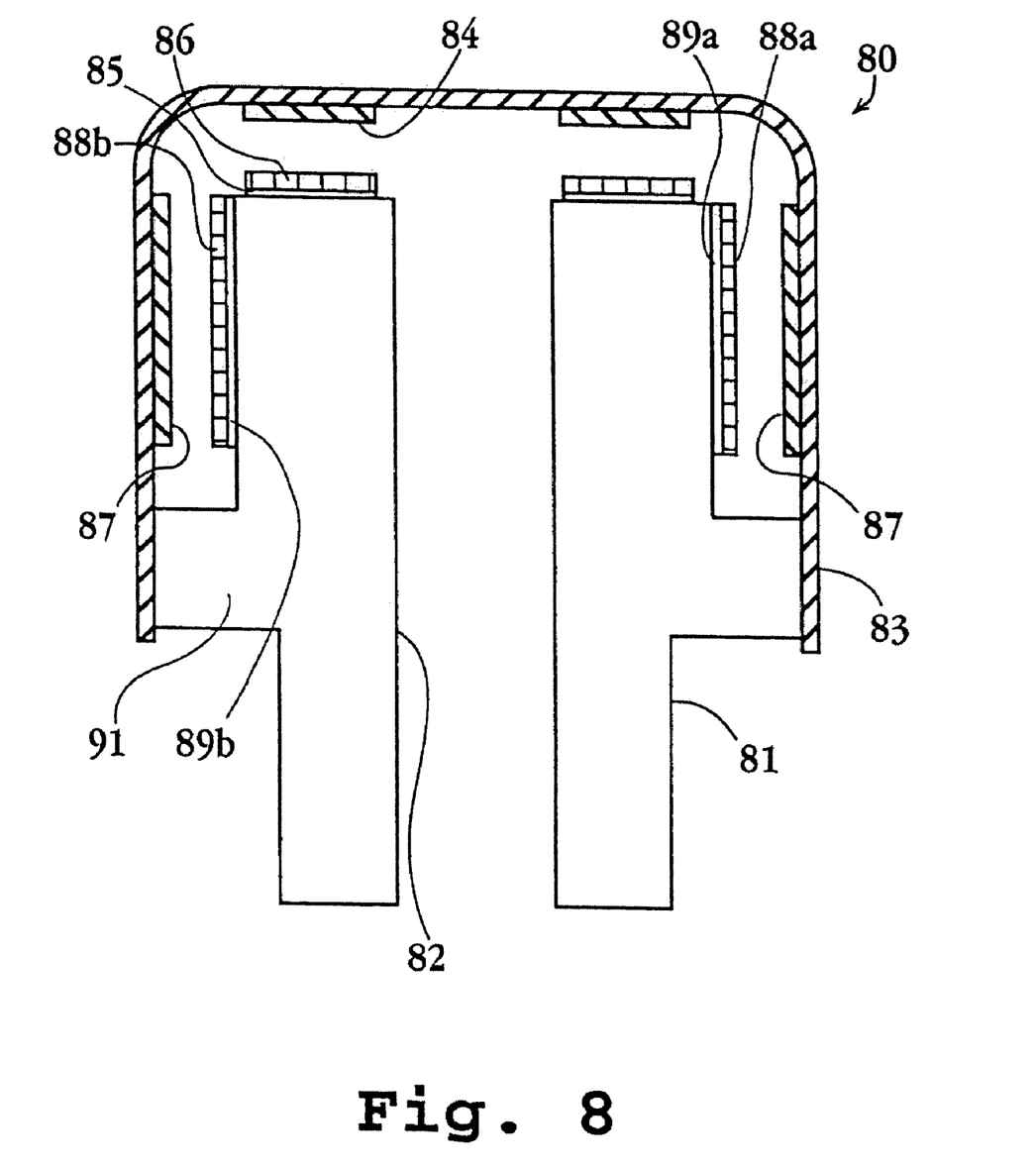
FIG. 8 illustrates, in simplified view, the cap region of a transducer capable of detecting both axial and lateral force components applied to the sensor.

FIG. 8 shows another embodiment of a sensor device 80 for use in the apparatus of the invention. The device shown here is designed to measure both axial pressure, along an axis normal to the contact face of the probe, and lateral direction, i.e., force applied to a side region of the probe. The device includes a rigid mechanical support 81 which is attached at its lower end in the figure to the distal end of the accessing tool, and which provides a central opening 82 through which the therapeutic effector, e.g., needle or optical fiber is received.

The device has a flexible cap 83 that is rigidly attached to a radially extending annular ring 91 in the support. The cap is formed of a flexible polymer or elastomer material or other flexible material that permits the cap to deform when pressure is applied to the cap, when the probe is in contact with the target tissue. Carried on an inner, upper surface of the cap is a preferably segmented annular electrode ring 84 positioned to contact an annular conductive elastomer member 86 of the type described above, when an axial pressure acts and distorts the upper surface of the cap. The elastomer member, in turn, is seated on an insulative spacer 85 that provides an electrical barrier between the elastomer and support, but which provides openings or notches through which the elastomer can be pressed, when an axial force acts on it, as described with reference to FIGS. 1–4.

In operation, when an axial force is applied to the cap, the cap is distorted to bring electrode ring 84 into contact with elastomer member 86, pushing the elastomer through spaces in the insulative spacer 85. This changes the resistance of a circuit containing the two electrodes and the elastomer member in proportion to the total contact area that the elastomer makes with the support electrode, and this change in resistance is recorded and displayed to the user.

Carried on the annular side region of the support is a plurality of insulative members, such as elastomeric members 88a, 88b, arranged circumferentially about the support. Typically, the device includes three such members, each member being carried on an insulative spacer, such as spacers 89a, 89b. Similarly, carried on the inner confronting surface of the cap is a segmented electrode 87 which is disposed to make contact with individual elastomer members 88a, 88b when side regions of the cap are distorted by side pressure and brought against the confronting elastomeric segments. Thus, side-directed pressure is detected, as above, by a change in the resistance in one or more of the side elastomer members, as the cap electrodes push against the elastomer member(s), forcing surface portions of the member(s) through openings in the spacers, and lowering the resistance of each associated circuit containing the affected elements. The user thus has information about axial pressure, from the change in resistance (impedance) in the upper-cap circuit, and information about angle of contact by the extent of asymmetry in measured resistances of the three side circuits.

In a purely mechanical device there may be disposed between the probe and the proximal end of the tool an elastic resilient support. Absent any surface contact, the probe's contact surface remains perpendicular to the thrust axis of the tool because of the elastic resilient support. Attached to the tool side of the probe are the ends of at least 3 or more flexible shafts running parallel or coherently through the tool length. These shafts run slidably through and protrude beyond lumens within the tool body beginning at the probe facing side of the proximal end of the tool and terminating as openings at the distal or user end of the tool. As the contact surface is deflected away from the thrust axis of the tool, the distance between the probe contact surface and the tool varies depending on the angle of deflection. The shaft, beneath where the distance between the contact surface of the probe and the proximal end of the tool is least, will protrude out more from the distal or user end of the tool, whereas the shafts opposite will recede into the tool at the distal or user end. Consequently, a user will be able to observe angular relation of the probe to the tool by observing the protrusion or withdrawal of the shafts, thereby the user could adjust the incident angle of the tool to achieve a balanced shaft display. One skilled in the art would readily recognize that many variations of this embodiment are possible, especially with respect to how the angular information is displayed to the user.

In another, multi-transducer embodiment, each pressure transducer is independently elastically and resiliently related to the contact surface, and another embodiment provides for each pressure transducer being mutually elastically and resiliently related to the contact surface.

In yet another embodiment, the monitor is operatively connected to the activator such that at a pre-selected measurement, the activator is activated thus causing the effector to activate. In a related embodiment, the monitor is operatively connected to the activator such that the activator can only be manually activated by the user when the monitor measures a predetermined measurement from the pressure transducer. In yet another related embodiment, the monitor does not affect the operability of the activator.

In yet another embodiment, the pressure transducer may respond to deflection by varying capacitance rather than resistance. Capacitance can be varied by sandwiching a pressure sensitive dielectric material between two electrodes. Alternatively, changes in pressure can be measured by varying inductance with inductor transducer device 90 illustrated in FIG. 9. As seen, the device includes a cap 94 which can move in an axial direction (the direction of arrow 100) toward and away from the relaxed (no-pressure) position shown in the figure, mounted for such axial movement on a support 92, which is carried on the distal end of the apparatus tool. The support provides an induction coil 99 formed of conductive wire windings 98 which are positioned adjacent a cylindrical permanent magnet 96 mounted on the cap.

Figure 9:
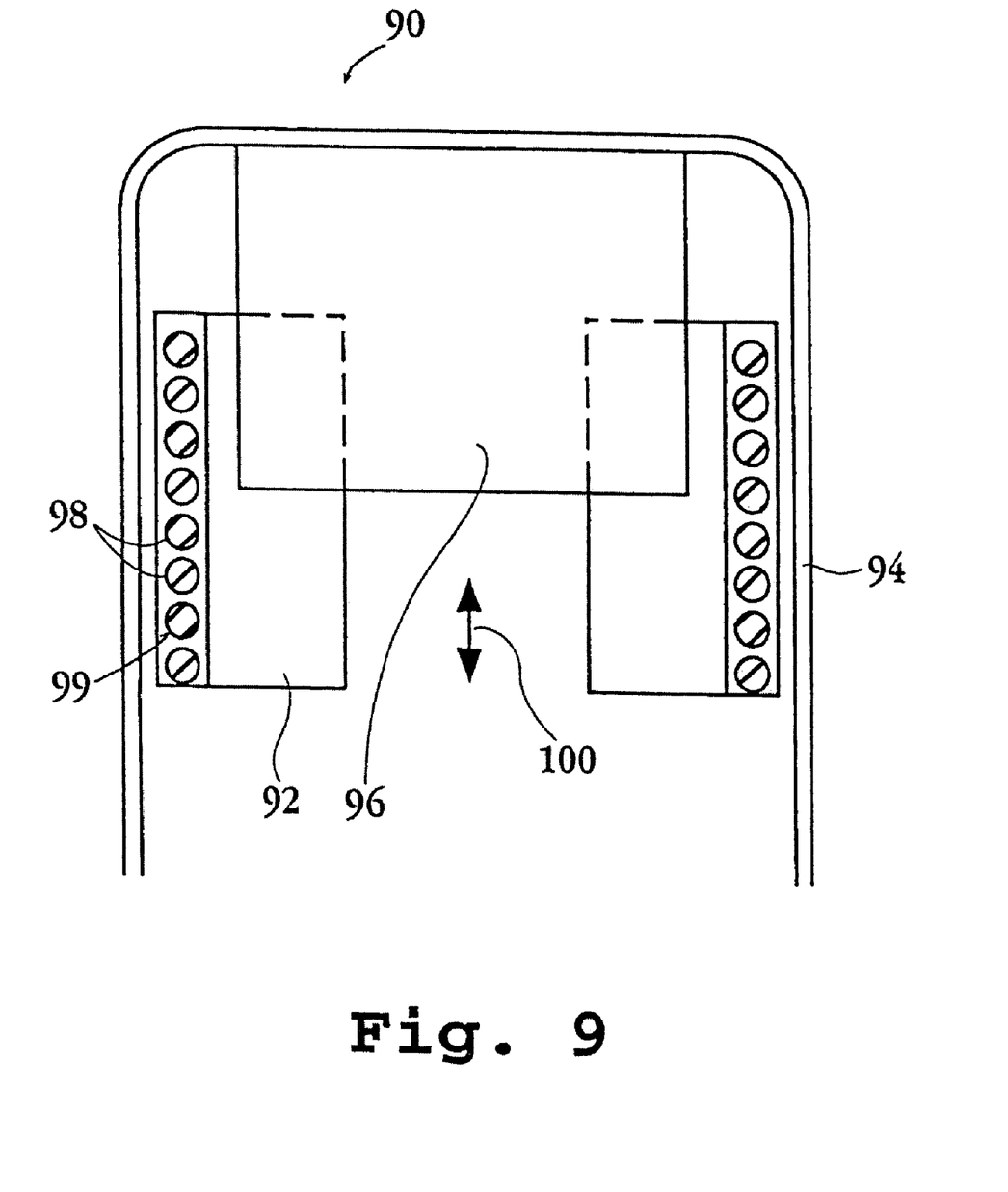
FIG. 9 illustrates an embodiment of the invention that measures force movement by electrical inductance, rather than by resistance.

Movement of the cap in the direction of arrow 100 carries magnet 96 past the inductive wires, producing a change in the inductance of the coil. Such changes can be monitored by incorporating the inductor into a LC or inductor-capacitor oscillating circuit and monitoring the change in the resonant frequency of the LC circuit.

In yet another embodiment, any transducer described herein may be combined with an ultrasonic transducer capable of detecting tissue density or thickness. For example, the ultrasonic transducer of Zanelli et al., U.S. Pat. No. 6,024,703, herein incorporated in its entirety by reference, discloses an ultrasound device for axial ranging. This would provide for the ability to limit the throw or depth that an effector element is permitted to penetrate into the patient tissue underlying the tissue surface thus avoiding either too shallow, thus ineffective penetration, or too deep and thus harmful penetration of the effector element.

As should be apparent from the foregoing description, the present invention, unlike fluoroscopic methods, provides force information such as but not limited to, force contact, magnitude and direction or incident angle with respect to the patient tissue surface, for catheter-based surgical procedures or other medical procedures where the degree of contact between the medical instrument and a surface of an anatomical structure is useful to know. In addition, such information may be provided in real-time and in a variety of formats using a low cost, disposable force contact transducer of the type disclosed herein. Such a transducer may be easily integrated into existing catheter tools, eliminating the need for extensive hardware/software interfaces.

While various embodiments of the invention have been illustrated and described, it will be evident to those skilled in the art in light of the foregoing disclosure that many further alternatives, modifications and variations are possible. For example, the insulator need not be a separate element but may be in the form of an insulative coating that is selectively applied to the conductive surface of the flange to permit the lower surface of the conductive elastomer to make contact with that conductive surface in accordance with the teachings of the invention. The invention disclosed herein is intended to embrace all such alternatives, modifications, and variations as may fall within the spirit and scope of the appended claims.

What is claimed:

1. A method of positioning a medical apparatus within a patient, comprising the steps of:
   (a) providing the medical apparatus composing an accessing tool, and a probe operatively connected with the accessing tool and located at the distal end of the accessing tool, wherein the probe comprises at least one pressure transducer;
   (b) inserting at least a portion of the accessing tool into the patient;
   (c) manipulating the accessing tool until the distal end of the accessing tool is adjacent a body site;
   (d) contacting the body site with the probe in a first position, thereby generating a first information signal from the at least one pressure transducer, wherein the first signal conveys the direction of a force applied by the body site on the probe; and
   (e) altering the position of the probe based at least in part on the first signal to a second position, thereby generating a second information signal.

2. The method of claim 1, wherein the second position is a desired position of the probe in relation to the body site.

3. The method of claim 1, further comprising the step of altering the positioning of the probe based at least in part on the second signal to a third position, thereby generating a third information signal.

4. The method of claim 1, wherein the information from at least the first signal conveys the incident angle of the probe relative to a surface of the body site.

5. The method of claim 1, wherein the first signal conveys the magnitude of a force applied by the body site on the probe.

6. The method of claim 1, wherein the apparatus further comprises a monitoring device, and wherein the first signal is displayed via the monitoring device.

7. The method of claim 1, wherein the probe further comprises at least one effector configured to provide a therapeutic effect.

8. The method of claim 7, wherein the probe further comprises an activator, and wherein the activator is associated with the effector such that the activation of the activator causes the effector to provide a therapeutic effect.

9. The method of claim 7, wherein the effector is configured to provide a therapeutic effect upon the reaching of a threshold force measured by the at least one pressure transducer.

10. The method of claim 1, wherein the accessing tool is inserted in step (b) using a catheter.

11. The method of claim 1, wherein the manipulation of the accessing tool in step (c) is aided by the use of x-ray fluoroscopy.

12. The method of claim 1, wherein the probe further comprises a support member, and wherein at least one pressure transducer is situated on the support member.

13. The method of claim 1, wherein the accessing tool further comprises a shaft located near the distal end of the accessing tool, and wherein the shaft is movable relative to the accessing tool.

14. The method of claim 13, wherein said pressure transducer includes (i) first and second conductors, (ii) an insulating layer adjacent the first conductor, said layer having one or more perforations therein, and (iii) a conductive elastomer disposed between the insulating layer and the second conductor and in contact with the second conductor, and the insulating layer and the conductive elastomer each (i) is mounted about the shaft, and (ii) at least partially surrounds the shaft.

15. The method of claim 14, wherein the insulating layer and the conductive elastomer each has an opening therein for receiving the shaft; and the shaft is inserted through the openings in the insulating layer and the conductive elastomer.

16. The method of claim 15, wherein the insulating layer is generally in the shape of a disk; and the opening in the insulating layer is disposed at or proximate the diametrical center of the insulating layer.

17. The method of claim 15, wherein the conductive elastomer has a generally circular configuration; and the opening in the conductive elastomer is disposed at or proximate the diametrical center of the conductive elastomer.

18. A method of positioning a medical apparatus within a patient, comprising the steps of:
   (a) providing the medical apparatus comprising an accessing tool, and a probe operatively connected with the accessing tool and located at the distal end of the accessing tool, wherein the probe comprises at least one pressure transducer, and at least one effector configured to provide a therapeutic effect upon the reaching of a threshold force measured by the at least one pressure transducer;
   (b) inserting at least a portion of the accessing tool into the patient;
   (c) manipulating the accessing tool until the distal end of the accessing tool is adjacent a body site;
   (d) contacting the body site with the probe in a first position, thereby generating a first information signal from the at least one pressure transducer; and
   (e) altering the position of the probe based at least in part on the first signal to a second position, thereby generating a second information signal.

19. The method of claim 18, wherein the information from at least the first signal conveys the incident angle of the probe relative to a surface of the body site.

20. The method of claim 18, wherein the first signal conveys the magnitude of a force applied by the body site on the probe.

21. The method of claim 18, wherein the apparatus further comprises a monitoring device, and wherein the first signal is displayed via the monitoring device.

22. The method of claim 18, wherein the probe further comprises a support member, and wherein at least one pressure transducer is situated on the support member.

23. The method of claim 18, wherein the probe further comprises an activator, and wherein the activator is associated with the effector such that the activation of the activator causes the effector to provide a therapeutic effect.

24. A method of positioning a medical apparatus within a patient, comprising the steps of:
   (a) providing the medical apparatus comprising an accessing tool comprising a shaft located near the distal end of the accessing tool and wherein the shaft is movable relative to the accessing tool, and a probe operatively connected with the accessing tool and located at the distal end of the accessing tool, wherein the probe comprises at least one pressure transducer, and wherein said pressure transducer includes (i) first and second conductors, (ii) an insulating layer adjacent the first conductor, said layer having one or more perforations therein, and (iii) a conductive elastomer disposed between the insulating layer and the second conductor and in contact with the second conductor; and the insulating layer and the conductive elastomer each (i) is mounted about the shaft, and (ii) at least partially surrounds the shaft;
   (b) inserting at least a portion of the accessing tool into the patient;
   (c) manipulating the accessing tool until the distal end of the accessing tool is adjacent a body site;
   (d) contacting the body site with the probe in a first position, thereby generating a first information signal from the at least one pressure transducer; and
   (e) altering the position of the probe based at least in part on the first signal to a second position, thereby generating a second information signal.

25. The method of claim 24, wherein the insulating layer and the conductive elastomer each has an opening therein for receiving the shaft; and the shaft is inserted through the openings in the insulating layer and the conductive elastomer.

26. The method of claim 25, wherein the insulating layer is generally in the shape of a disk; and the opening in the insulating layer is disposed at or proximate the diametrical center of the insulating layer.

27. The method of claim 25, wherein the conductive elastomer has a generally circular configuration; and the opening in the conductive elastomer is disposed at or proximate the diametrical center of the conductive elastomer.

* * * * *